United States Patent [19]
Fleury et al.

[11] Patent Number: 5,490,296
[45] Date of Patent: Feb. 13, 1996

[54] HEIGHT-ADJUSTABLE BED

[75] Inventors: Christophe Fleury, Guyancourt; Christian Pare, Plaisir, both of France

[73] Assignee: Sopha Medical, Paris, France

[21] Appl. No.: 244,941

[22] PCT Filed: Dec. 17, 1992

[86] PCT No.: PCT/FR92/01199

§ 371 Date: Oct. 5, 1994

§ 102(e) Date: Oct. 5, 1994

[87] PCT Pub. No.: WO93/11705

PCT Pub. Date: Jun. 24, 1993

[30] Foreign Application Priority Data

Dec. 17, 1991 [FR] France .................................. 91 15658

[51] Int. Cl.[6] ................................................ A47B 13/00
[52] U.S. Cl. ........................................ 5/601; 5/611; 5/86.1
[58] Field of Search ............................. 5/611, 601, 86.1; 378/195; 254/47, 4 R, 4 B, 4 C

[56] References Cited

U.S. PATENT DOCUMENTS

| | | | |
|---|---|---|---|
| 3,830,466 | 8/1974 | Rasmussen | 254/47 |
| 4,836,520 | 6/1989 | Span | 5/611 |
| 4,912,754 | 3/1990 | Van Steenburg | |
| 5,048,069 | 9/1991 | Siczek | |
| 5,067,145 | 11/1991 | Siczek et al. | |
| 5,131,105 | 7/1992 | Harrawood et al. | 5/611 |
| 5,237,600 | 8/1993 | Kamata | 5/611 |

FOREIGN PATENT DOCUMENTS 0283083  9/1988  European Pat. Off. .

Primary Examiner—Michael J. Milano
Attorney, Agent, or Firm—Browdy and Neimark

[57] ABSTRACT

The invention relates to a device for an examination bed which is adjustable in height, used particularly for a tomography by scintigraphy. The object of the invention is to enable a large amplitude displacement of the bed along the vertical. It allows to situate the bed, at the maximum position, at a height with respect to the to the ground more than twice higher than the low position. An intermediary carriage (14) is intercalculated between the patient support (13) and the pedestal (15) of the device. The carriage (14) and the patient support (13) move simultaneously and along the vertical with respect to the pedestal (15) of the device. By using a chain (20) whose extremities (26, 27) are fixed to the pedestal (15) and to the patient support (13), and which passes on top of a pulley (19) fixed to the intermediary carriage (14), the patient support (13) is raised by lifting the intermediary carriage (14).

20 Claims, 3 Drawing Sheets

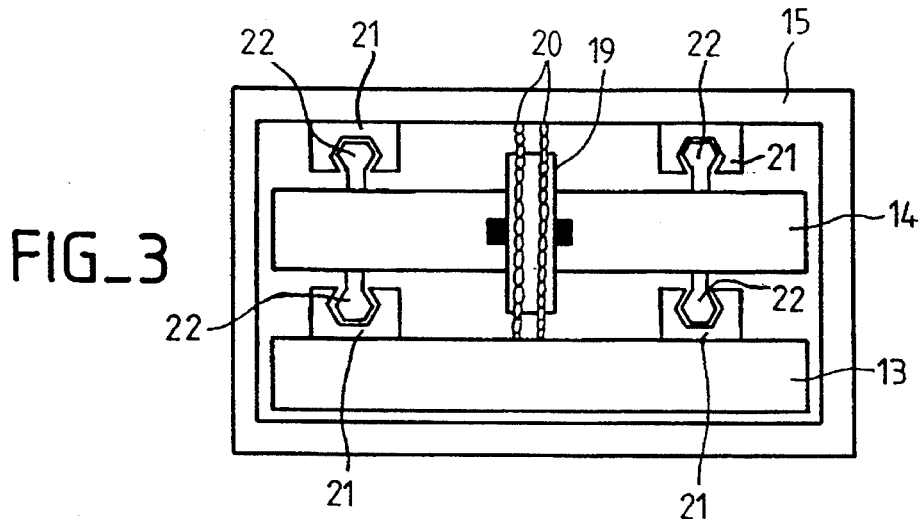
FIG_3
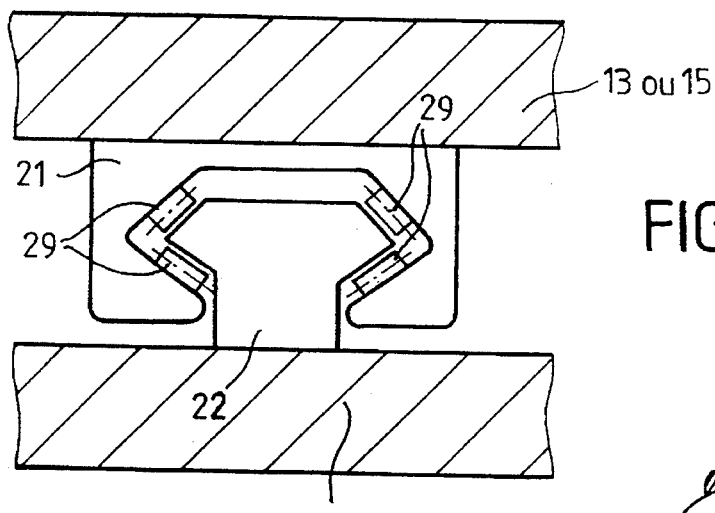
FIG_4
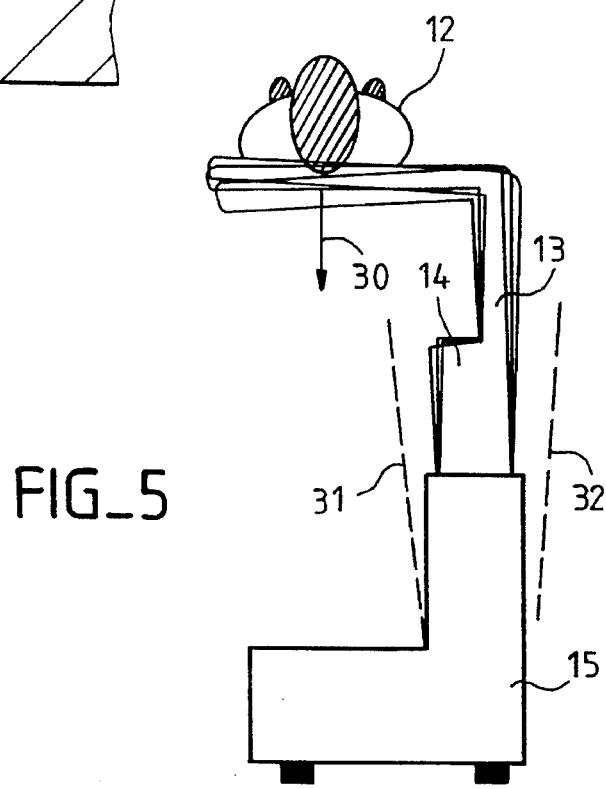
FIG_5

HEIGHT-ADJUSTABLE BED

BACKGROUND OF THE INVENTION

1. Field of the Invention

An object of the present invention is an examination bed that can be adjusted in height, used for medical purposes and especially for tomography by scintigraphy. Its object is to enable a largeamplitude vertical shifting of the bed. It enables the bed to be located, in the maximum position, at a height from the ground that is twice as great as its low position.

2. Description of the Prior Art

At present, for tomography by scintigraphy of organs of the human body, a patient to be examined is made to recline on an examination bed, the organ to be examined being placed before a detector of a gamma camera. The tomography examination consists in acquiring one image, in projection, of the organ per angle of view, for a large number of angles of view. These angles of view are evenly spaced out over an angular sector of at least 180°. They are obtained by making the detector of the gamma camera pivot about the patient. It is then possible to use computation algorithms to reconstitute the image of the volume examined from the images in projection.

In an as yet unpublished French patent application No. 91 06962, filed on 7th Jun. 1991, a gamma camera with two detector heads is used for the tomography of organs of the human body, the point aimed at by the detector heads being offset with respect to the rotational axis of the gamma camera. To this end, the detector heads are made to perform angular motions that are symmetrical in relation to the horizontal plane. This implies that the fields of detection of the two detector heads are no longer parallel. Then, the gamma camera and, consequently, the detector heads are made to pivot, one and the same location in the human body being kept as the point aimed at during the rotation.

However, since the point aimed at is offset in relation to the rotational axis of the gamma camera, the gamma camera must be moved in a lateral translational motion while the bed is moved in an ascending motion.

Nevertheless, a major problem arises for it is necessary, in this case, to provide for a bed whose low position is located at 55 centimeters above the ground while its high position is at about 120 centimeters, the shifting of this bed being done vertically. Now, at present, the beds generally used in hospitals are beds whose underframe is X-shaped. These beds have a first drawback which is that they rise not vertically but in describing a circular arc. A second drawback arises out of the fact that the X-shaped underframe leaves a clearance under the bed that is not always the same depending on whether the bed is in the high position or in the low position. Apart from this approach, there is no possibility of having examination beds whose range of elevation has a factor of two or even more. Furthermore, given the weights involved (in the range of a ton given the safety coefficients), any structure that can be envisaged is either too heavy or too flimsy.

SUMMARY AND OBJECTIVE OF THE INVENTION

To overcome these problems, the idea that has come up in the present invention is that of interposing an intermediate carriage between a carriage supporting the bed, called the patient support, and the pedestal of the device. These two carriages shift simultaneously and vertically with respect to the pedestal of the device. By means of a chain, or another such device vertically with respect to the pedestal of the device. By means of a chain, or another such device that has its ends fixed to the pedestal and the patient support and passes above a pulley fixed to the intermediate carriage, the patient support is raised by the lifting of the intermediate carriage. This enables a shifting that is firstly vertical and secondly has a large amplitude because the shifting of the patient support is equal to twice that of the intermediate carriage. It is therefore enough to shift the intermediate carriage by about 30 centimeters, which can be done in practice by means of a screw, to obtain a shift of the patient support by about 60 centimeters so that the bed is positioned in the high position at about 120 centimeters. The invention therefore meets the constraints that are laid down.

Thus, an object of the invention is an examination bed, adjustable in height, and in an overhanging position, used in a mobile way for medical purposes, notably for tomography by scintigraphy, comprising a pedestal, a motor and a patient support.

characterized in that it enables a large-amplitude shifting of the patient support along the vertical, said bed comprising:

an intermediate carraige means, actuated by the motor, to push the intermediate carriage vertically by makint it slide with respect to the pedestal a patient support shifting vertically along the intermediate carriage a pulley fixed to the intermediate carriage supporting a chain whose ends and are fixed to the pedestal and to the patient support in order to be capable of raising the patient support when the means to push the intermediate carriage raise this carriage and, consequently, the pulley the pedestal and the patient support comprising skids that slide along four vertical rails fixed to the intermediate carriage, two on the pedestal side and two on the patient support side, in order to enable, firstly, the vertical shifting of the intermediate carriage with respect to the pedestal and, secondly that of the patient support with respect to the intermediate carriage the rails having a hexagon-sectioned shape so that the skids cooperate respectively with at least four of the sides of the hexagonal section as to be capable of bearing the patient support and the intermediate carriage in directions perpendicular to the sides of the hexagon so as to prevent the tilting of the patient support.

BRIEF DESCRIPTION OF THE DRAWINGS

The invention will be understood more clearly from the following description and from the examination of the accompanying figures. These figures are given purely by way of an indication and in no way restrict the scope of the invention. Of these figures:

FIGS. 2 and 3 show sectional views of the bed according to the invention, seen in a side view and a top view;

FIG. 4 exemplifies a configuration of the rails and skids enabling, firstly, the shifting of the intermediate carriage with respect to the pedestal and, secondly, the shifting of the patient support with respect to the intermediate carriage so that it is suited to the implementation of the invention; and FIG. 5 shows a bed according to the invention, inclined under the effect of the weight of a patient reclining on the patient support.

DESCRIPTION OF THE PREFERRED EMBODIMENT(S)

Figure 1:
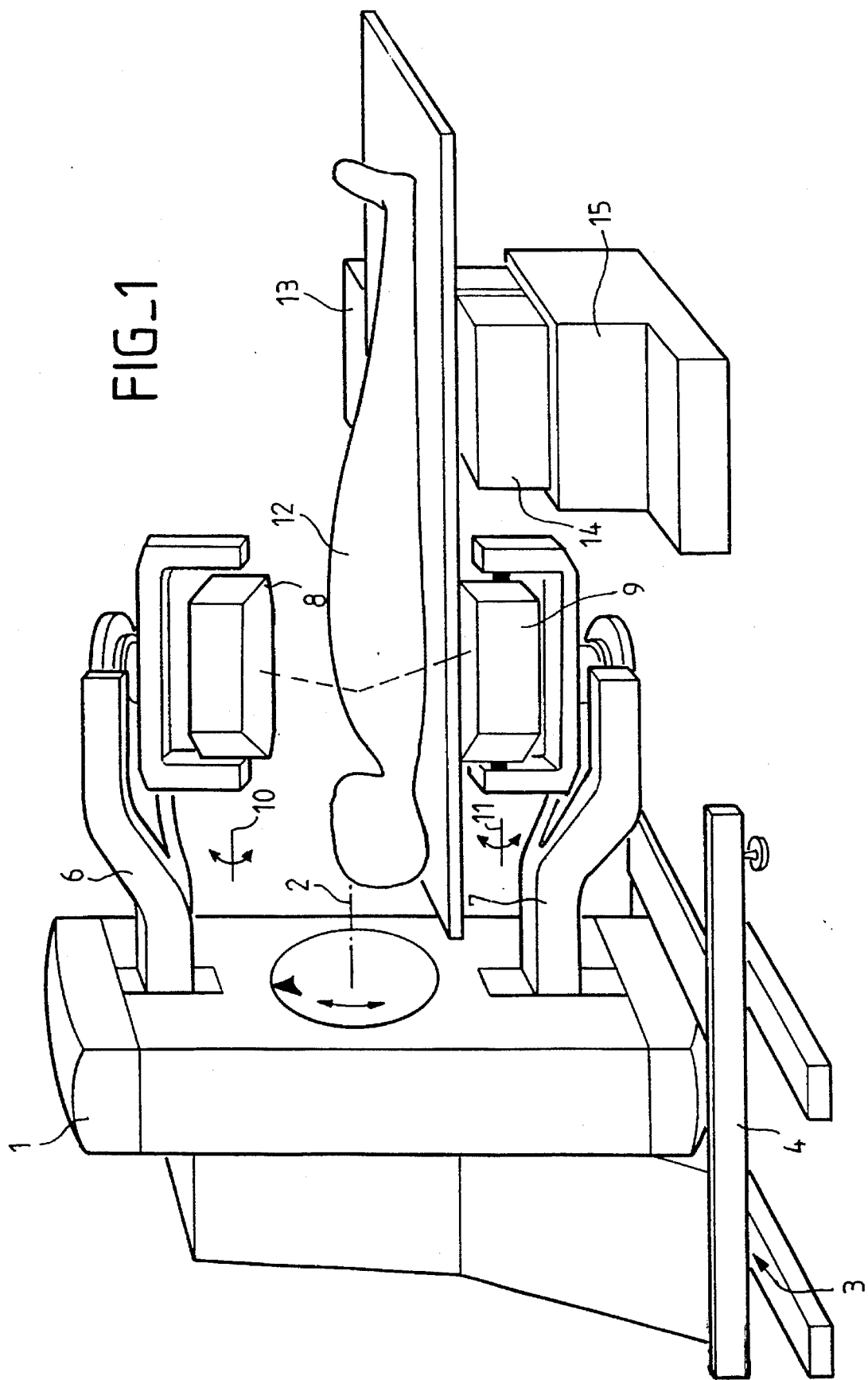
FIG. 1 shows a view in perspective of a bed according to the invention, before an examination apparatus.

FIG. 1 shows a patient 12 reclining on a patient support 13, an intermediate carriage 14 and a pedestal 15 according to the invention. The patient support 13 is, in one example, mounted so as to be overhanging the pedestal 15. The patient support substantially has an inverted L-shape. The pedestal is L-shaped. A detector of a gamma camera is placed before the patient 12. It has a rotating base 1, capable of rotating about a rotational axis 2. The base is held rotationally on a frame 3 provided with a foot 4. The base 1 has two bearing arms, 6 and 7 respectively, each bearing a detector head, 8 and 9 respectively, of the gamma camera. These detector heads can pivot about axes 10 and 11 parallel to the axis 2. This motion is hereinafter called an angular motion.

During an examination, the angular motion of the heads is fixed for the entire duration of the examination. The gamma camera and the detector heads 8 and 9 are made to pivot about the patient 12. Since the detector heads 8 and 9 are not horizontal, the point P in the human body at which they are aimed is offset with respect to the rotational axis 2. Consequently, so that the same point P is always aimed at, it is necessary, during the rotation of the gamma camera, to move the gamma camera with a lateral translational motion while the patient support 13 is moved with an ascending motion. In this use, the ascending motion should have a great range.

The ascending motion of the patient support 13 is obtained, firstly, through the vertical shifting of the intermediate carriage 14 with respect to the pedestal 15 and, secondly, through the motion of the patient support 13 with respect to the intermediate carriage 14.

Figure 2:
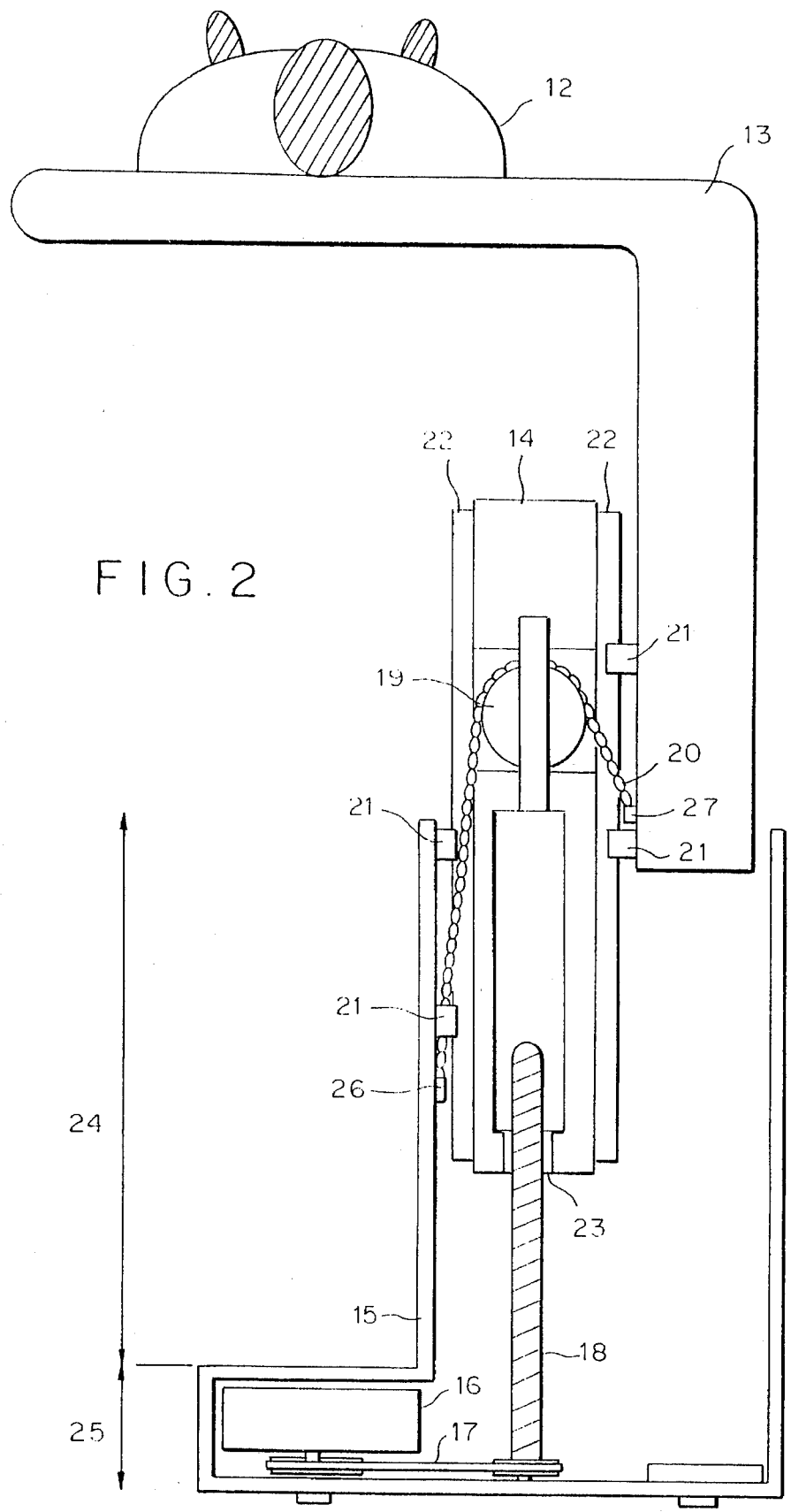

FIG. 2 shows a motor 16 that can be used, by means of a belt 17, to actuate means 18 for raising the intermediate carriage 14. A pulley 19 is fixed to the intermediate carriage 14. A chain 20 passes over the pulley. The ends 26 and 27 of the chain are hooked to the pedestal 15 and to the patient support 13. The intermediate carriage 14 and the patient support 13 are shifted by means of skids 21 that slide along rails 22.

In the invention, the raising means 18 are actuated to raise the intermediate carriage 14. The device used notably is a worm screw 18 that is screwed into a nut 23 fixed to the lower part of the intermediate carriage. The rotational motion of the screw 18 is prompted by the motor 16 and is transmitted to the screw 18 by means of a belt 17. It would also have been possible to use a screw engaged in a nut fixedly joined to the pedestal 15. This screw would give a thrust, from underneath, to the intermediate carriage 14 which would have been laid on a skid at the end of the screw (this is not shown in the figures).

The raising of the intermediate carriage 14 causes the raising also of the pulley 19. In an upward motion, the pulley 19 carries along the end 27 of the chain 20 fixed to the patient support 13. Thus, when the intermediate carriage 14 is shifted along a certain length, the patient support 13 gets shifted by twice the distance. Indeed, since the chain 20 is held to the pedestal 15 by its end 26, the raising of the carriage 14 causes the chain 20 to be wound on the pulley 19.

To meet the constraints laid down and mentioned here above, the following dimensions are used. These dimensions are given purely by way of an indication and in no way restrict the scope of the invention. The vertical part of the pedestal 15, represented by the arrow 24, has a length of 45 centimeters. The part represented by the base of the pedestal, arrow 25, has a length of 10 centimeters. Thus, when the patient support 13 and the intermediate carriage 14 are completely inside the pedestal 15, a low position of 55 centimeters (45+10) is obtained. Furthermore, rails 22 having a length of 55 centimeters are used. However, the shifting of the intermediate carriage 14 with respect to the pedestal 15 and the shifting of the patient support 13 with respect to the intermediate carriage 14 are limited to a length of 32 centimeters. By totalling these two shifts and the minimum height, the patient support 13 can be made to rise to a maximum height of about 120 centimeters (55+32*2) above the ground. In the maximum position, each rail 22 then has a minimum length along 22 centimeters laid against the pedestal 15 and the patient support 13. To this end, the height of the intermediate carriage 14 too is in the range of 55 centimeters.

The values of the load stresses are increased at great height. For example, it is assumed that the mass of the patient 12 and the patient support 13 cannot exceed 200 kg. It is assumed that the patient support 13 is mounted in an overhanging position. It is assumed that a normal safety coefficient is about six. It must therefore be seen to it that the entire unit can support up to 1.2 tons. The fact that each rail 22 has a bearing length, in the high position, of 23 centimeters then makes it possible to withstand these stresses and meet the conditions of vertical lifting.

As for the chain 20, it should preferably be of a type such that, in the low position, the part of the chain between the pulley 19 and the fastening point 27 of this chain 20 to the patient support 13 has a length substantially equal to 32 centimeters so that the patient support 13 can move by 32 centimeters with respect to the intermediate carriage 14. This condition makes it necessary for the pulley 19 to be fixed at more than 32 centimeters above the lower part of the intermediate carriage 14 and for the fastening point 27 to the patient support 13 to be located at about 32 centimeters beneath the pulley 19 when this pulley is in the low position. This condition, once achieved, means that the chain 20 has a length necessarily greater than 32 centimeters and thus enables the intermediate carriage 14 to move by 32 centimeters. The other end 26 of the chain 20, the one fixed to the pedestal 15, can be located at any height whatsoever on the pedestal 15. Preferably, the chain 20 is fixed as close as possible to the low position of the pulley 19 in order to obtain a gain in chain length.

The pulley 19 should be fixed at a point at least 32 centimeters above the lower part of the intermediate carriage 14. As can be seen in FIG. 2, at the position in which the pulley 19 is fixed, it is necessary to provide for a passage of the chain through the intermediate carriage 14 while keeping the continuity of the rails 22.

In one example, the pulley 19 is fixed at about 32 centimeters above the lower part of the intermediate carriage 14. This has the advantage wherein, when placed at this height, it fulfils the role of a stop element. Indeed, since the fastening 27 of the chain 20 to the patient support 13 can never be located at a level greater than that of the pulley 19, this shifting of the patient support 13 with respect to the intermediate carriage 14 is limited by the position of the pulley 19 to 32 centimeters.

To adjust or modify the maximum and minimum positions of the patient support 13 by a few centimeters, there is provision for a height-wise adjustment of the pulley 19 and of the fastening 27 of the chain 20 to the patient support 13. For this purpose, the invention uses rails (not shown in the figure) that are fixed respectively to the intermediate carriage 14 and to the patient support 13, the pulley 19 and the fastening 27 being moved along these rails if necessary.

Furthermore, for reasons of safety, the invention uses a double chain 20, shown in FIG. 3, namely a chain having two sets of enchained links placed side by side. It is also possible to use two pulleys around which two distinct chains pass. Again for the same reasons, the use of belts is ruled out for they are break more easily than chains.

The chain may be replaced by another device. It is possible, for example, to design a system where the pedestal 15 and the patient support 13 have facing racks. A toothed wheel is engaged in both these racks at the same time. It rotates on a shaft fixed to the intermediate carriage 14. It makes the patient support 13 rise in relation to the intermediate carriage 14 when this intermediate carriage 14 is pushed upwards. This has not been shown in the figures.

As can be seen in FIG. 3, which shows the same elements in a sectional view, four rails 22 are fixed to the intermediate carriage 14 (two on the pedestal 15 side and two on the patient support 13 side). They are notably of the THK type. This figure also shows four skids 21. In the practical embodiment, these skids are eight in number. The other four skids are not shown because they are located at a level below the plane of the sectional view of FIG. 3. Of the skids 21, half are fixed to the patient support 13 and the other half to the pedestal 15. The skids 21 could also be fixed to the intermediate carriage 14 and the rails 22 to the pedestal 15 and the patient support 13. It amounts to the same thing. In order that they may be useful when the patient support 13 is in the high position, the four skids 21 of the pedestal 15 are located at the top of the pedestal 15 while those of the patient support 13 are located at the bottom of the patient support 13. In one example, the skids 21 of the patient support 13 as well as those of the pedestal 15 are spaced out from one another by 15 centimeters in height and 25 centimeters in width.

FIG. 4 shows that the THK-type rails 22 have hexagonal profiles. Thus, they enable the skids 21 to exert forces in all three directions perpendicular to the sides of the hexagon. The forces prevent the tilting of the patient support 13. This is an advantage as compared to rectangular-type slide-channels which work in only two directions.

The skids 21 have removable and interchangeable bearings 29. If bigger bearings 29 are used, the clearance between the rails 22 and the skids 21 is reduced. As a result, the assembly, namely the intermediate carriage 14, the patient support 13 and the pedestal 15, is further consolidated. The choice of bigger bearings 29 must be done as a function of the power available at the motor 16. The bigger bearings 29 exert greater resistance. The advantage of the THK type rails 22 is therefore put to good use here. With bigger bearings 29, greater rigidity of the assembly is obtained while preventing the intermediate carriage 14 from being placed flat against the pedestal 15 and the patient support 13 against the intermediate carriage 14. With the hexagonal profile of the THK type rails 22, two faces of the skids 21 exert reaction forces on each other on one and the same rail.

As indicated further above, the patient support 13 is generally mounted in a position of overhanging the pedestal 15. Hence, under the effect of the weight of the patient 12 represented in FIG. 5 by the arrow 30, the intermediate carriage 14 and the patient support 13 tend to tilt along a direction 31 (shown in dashes) that is offset with respect to the vertical. To overcome this problem, the intermediate carriage 14 and the patient support 13 are designed to rise, when there is no patient 12 on the patient support 13, along a direction 32 (shown in dashes), that is slightly offset in a slanting direction on the other side with respect to the vertical. It rises vertically if a patient 12 is reclining on the patient support 13, under the effect of this patient's weight 30. This rise is substantially vertical for all the levels of elevation.

We claim:

1. Examination bed, adjustable in height, and in an overhanging position, used in a mobile way for medical purposes, notably for tomography by scintigraphy, comprising a pedestal (15), a motor (16) and a patient support (13), characterized in that it enables a large-amplitude shifting of the patient support (13) along the vertical, said bed comprising:

an intermediate carriage (14)

means (18), actuated by the motor (16), to push the intermediate carriage (14) vertically by making it slide with respect to the pedestal (15)

a patient support (13) shifting vertically along the intermediate carriage (14)

a pulley (19) fixed to the intermediate carriage (14) supporting a chain (20) whose ends (26) (27) are fixed to the pedestal (15) and to the patient support (13) in order to be capable of raising the patient support (13) when the means (18) to push the intermediate carriage (14) raise this carriage (14) and, consequently, the pulley (19)

the pedestal (15) and the patient support (13) comprising skids (21) that slide along four vertical rails (22) fixed to the intermediate carriage (14), two on the pedestal (15) side and two on the patient support (13) side, in order to enable, firstly, the vertical shifting of the intermediate carriage (14) with respect to the pedestal (15) and, secondly, that of the patient support (13) with respect to the intermediate carriage (14)

the rails (22) having a hexagon-sectioned shape so that the skids (21) cooperate respectively with at least four of the sides of the hexagonal section as to be capable of bearing the patient support (13) and the intermediate carriage (14) in directions perpendicular to the sides of the hexagon so as to prevent the tilting of the patient support (13).

2. Bed according to claim 1, characterized in that the means (18) to push the intermediate carriage (14) comprise a screw (18) that lifts the intermediate carriage (14).

3. Bed according to claim 2 characterized in that the means (18) to push the intermediate carriage (14) comprise a worm screw (18) that lifts the intermediate carriage by getting screwed into a nut (23) fixed to the lower part of the intermediate carriage (4).

4. Bed according to claim 3, characterized in that the skids (21) have removable and interchangeable bearings (29) in order to enable a reduction of the clearance between the rails (22) and the skids (21).

5. Bed according to claim 4, characterized in that the pulley (19) and the fastening point (27) of the chain (20) to the patient support (13) are adjustable in height.

6. Bed according to claim 5, characterized in that the fastening (26) of the chain (20) to the pedestal (15) is located in a high position, close to the pulley (19), to enable the length of the chain (20) to be shortened.

7. Bed according to claim 6, characterized in that the patient support (13) is mounted so that it is in an overhanging position with respect to the pedestal (15).

8. Bed according to claim 7, characterized in that the intermediate carriage (14) and the patient support (13) are oriented so as to rise, when there is no patient (12) on the patient support (13), along an axis (32) that is slightly offset slantwise with respect to the vertical so that they rise vertically if a patient (12) is reclining on top, under the effect of his or her weight (30).

9. Bed according to claim 1 characterized in that the means (18) to push the intermediate carriage (14) comprise a worm screw (18) that lifts the intermediate carriage by getting screwed into a nut (23) fixed to the lower part of the intermediate carriage (14).

10. Bed according to claim 1, characterized in that the skids (21) have removable and interchangeable bearings (29) in order to enable a reduction of the clearance between the rails (22) and the skids (21).

11. Bed according to claim 1, characterized in that the pulley (19) and the fastening point (27) of the chain (20) to the patient support (13) are adjustable in height.

12. Bed according to claim 1, characterized in that the fastening (26) of the chain (20) to the pedestal (15) is located in a high position, close to the pulley (19), to enable the length of the chain (20) to be shortened.

13. Bed according to claim 1, characterized in that the patient support (13) is mounted so that it is in an overhanging position with respect to the pedestal (15).

14. Bed according to claim 1, characterized in that the intermediate carriage (14) and the patient support (13) are oriented so as to rise, when there is no patient (12) on the patient support (13), along an axis (32) that is slightly offset slantwise with respect to the vertical so that they rise vertically if a patient (12) is reclining on top, under the effect of his or her weight (30).

15. Bed according to claim 7, characterized in that the skids (21) have removable and interchangeable bearings (29) in order to enable a reduction of the clearance between the rails (22) and the skids (21).

16. Bed according to claim 2, characterized in that the pulley (19) and the fastening point (27) of the chain (20) to the patient support (13) are adjustable in height.

17. Bed according to claim 2, characterized in that the fastening (26) of the chain (20) to the pedestal (15) is located in a high position, close to the pulley (19), to enable the length of the chain (20) to be shortened.

18. Bed according to claim 2, characterized in that the patient support (13) is mounted so that it is in an overhanging position with respect to the pedestal (15).

19. Bed according to claim 2, characterized in that the intermediate carriage (14) and the patient support (13) are oriented so as to rise, when there is no patient (12) on the patient support (13), along an axis (32) that is slightly offset slantwise with respect to the vertical so that they rise vertically if a patient (12) is reclining on top, under the effect of his or her weight (30).

20. Bed according to claim 5, characterized in that the intermediate carriage (14) and the patient support (13) are oriented so as to rise, when there is no patient (12) on the patient support (13), along an axis (32) that is slightly offset slantwise with respect to the vertical so that they rise vertically if a patient (12) is reclining on top, under the effect of his or her weight (30).

* * * * *